United States Patent [19]

Fliri et al.

[11] Patent Number: 4,503,221
[45] Date of Patent: Mar. 5, 1985

[54] PROCESS FOR CEPHALOSPORANIC ACID DERIVATIVES AND INTERMEDIATE THEREFOR

[75] Inventors: Hans Fliri; Helmut Hamberger, both of Vienna, Austria

[73] Assignee: Sandoz Ltd., Basel, Switzerland

[21] Appl. No.: 505,807

[22] Filed: Jun. 20, 1983

Related U.S. Application Data

[62] Division of Ser. No. 340,435, Jan. 18, 1982, Pat. No. 4,440,767.

[30] Foreign Application Priority Data

Jan. 19, 1981 [CH] Switzerland .................... 317/81

[51] Int. Cl.³ .................. C07D 417/12; C07D 501/04
[52] U.S. Cl. ........................................ 544/27; 548/170
[58] Field of Search ........................... 544/27; 548/170

[56] References Cited

U.S. PATENT DOCUMENTS

| 2,090,242 | 8/1937 | Teppema et al. ............... 548/170 |
| 4,024,137 | 5/1977 | Cook et al. ..................... 544/27 |
| 4,314,059 | 2/1982 | Shibuya et al. ................. 544/27 |
| 4,316,024 | 2/1982 | Iimura et al. ................... 544/27 |
| 4,351,947 | 9/1982 | Shibuya et al. ................. 544/26 |
| 4,456,754 | 6/1984 | Murakami et al. .............. 544/27 |

FOREIGN PATENT DOCUMENTS

881641   8/1980   Belgium .

Primary Examiner—Paul M. Coughlan, Jr.
Attorney, Agent, or Firm—Gerald D. Sharkin; Richard E. Vila; Frederick H. Weinfeld

[57] ABSTRACT

The process for preparing cephalosporanic acid derivatives

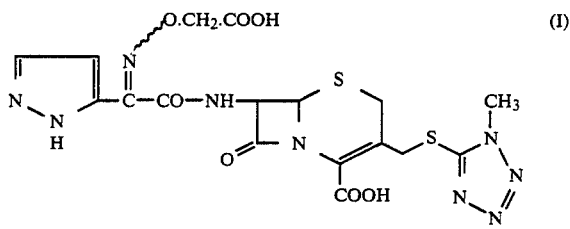

and salts thereof with bases as well as solvates thereof, comprising reacting a compound of the formula II:

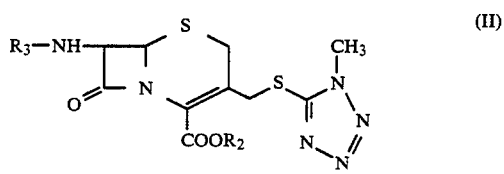

wherein $R_3$ represents hydrogen or an amino protecting group and $R_2$ represents hydrogen, an easily removable ester group or other carboxyl protecting group, with a compound of formula IIIa,

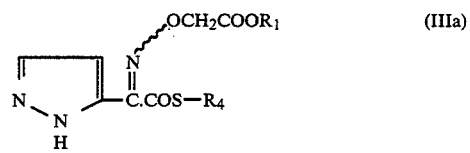

wherein $R_1$ represents hydrogen, an easily removable ester group or other carboxyl protecting group, and $R_4$ is a 2-benzothiazol group and salts thereof with bases, and if required removing any ester group or protecting group.

2 Claims, No Drawings

PROCESS FOR CEPHALOSPORANIC ACID DERIVATIVES AND INTERMEDIATE THEREFOR

This is a division of application Ser. No. 340,435, filed Jan. 18, 1982, now U.S. Pat. No. 4,440,767.

The present invention concerns novel derivatives of cephalosporanic acid, processes for their production and their use as pharmaceuticals.

British patent application No. 8004696 (Publication No. 2046734A) discloses a wide range of cephalosporanic acid derivatives having anti-microbial properties.

The present invention provides a novel cephalosporanic acid derivative and salts thereof, falling within the scope of said British Patent Application, but not disclosed therein. The compounds of the invention surprisingly exhibit particularly advantageous anti-microbial properties including a high level of activity and a synergistic effect on PMNs as hereinafter described.

More particularly the invention provides 7-[(carboxymethoximino)-1H-pyrazol-3-yl-acetyl]amino-3-desacetoxy-3-(1-methyl-1H-tetrazol-5-yl-thio)cephalosporanic acid of formula I,

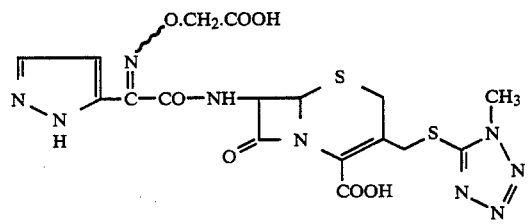

and salts thereof with bases as well as solvates thereof.

The compound of formula I can also be referred to as 7-[α[(carboxymethoxy)imino]-1H-pyrazol-3-yl-acetyl]amino-3-[(1-methyl-1H-tetrazol-5-yl)thiomethyl]-8-oxo-5-thia-1-azabicyclo[4.2.0]oct-2-ene-2-carboxylic acid.

According to the invention the compounds of the invention may be prepared by reacting a compound of formula II,

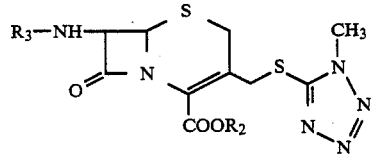

wherein $R_3$ represents hydrogen or an amino protecting group and $R_2$ represents hydrogen, an easily removable ester group or other carboxyl protecting group, with a compound of formula III,

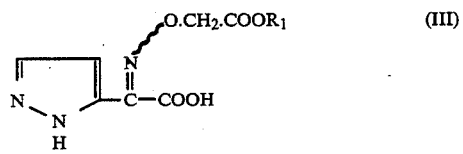

wherein $R_1$ represents hydrogen, an easily removable ester group or other carboxyl protecting group, or a reactive derivative thereof, and if required removing any ester group or protecting group present in the compound of formula I thus obtained to produce a compound of formula I in free acid form, and recovering the compound of formula I in free acid form or in the form of a salt thereof with a base or in the form of a solvate.

The compounds of formulae II and III can also be employed, if desired and where appropriate in the form of a salt thereof with a base or in the form of a solvate.

Suitable reactive derivatives of the acid of formula III include acid halides or acid anhydrides, for example with pivalic acid or carbonic acid half-esters, activated complexes with dimethyl formamide/phosphorous oxychloride, acid azides or activated esters, for example derived from phenols, cyclic N-hydroxyimides or heterocyclic thiols, e.g. 2-pyridinethiol, 2,2'-dithiopyridine or particularly bis-benzothiazolyl disulphide.

The process is suitably effected by dissolving or suspending the compound III or derivative thereof in an inert solvent, such as chlorinated hydrocarbon, e.g. dichloromethane, or an acid ester, e.g. ethyl acetate. This solution or suspension is then suitably added to a solution or suspension of the compound II in an inert solvent, e.g. an acid ester, such as ethyl acetate, or an aromatic hydrocarbon, e.g. toluene. The process is conveniently effected at a temperature of, e.g. −20° C. to room temperature. When the compound of formula III is used in free acid form, a condensation agent, such as dicyclohexyl carbodiimide or carboxydiimidazole is suitably added.

Where a compound of formula I is desired, in which the COOH group of the cephalosporanic acid is in free form, it is convenient to protect the carboxylic acid function in the starting material of formula II prior to reaction with the compound of formula III or derivative thereof. Conventional methods of protection may be employed.

Examples of easily removable esters and/or protecting groups are tert.butyl, benzhydryl, ethyl, acetoxymethyl, pivaloyloxymethyl or trimethylsilyl.

Such groups can be introduced at any time during preparation of the starting materials in conventional manner such as by esterification, e.g. in the case of trimethylsilyl by reaction with N,O-bis-trimethylsilylacetamide.

Removal of esters and protecting groups can be carried out according to conventional methods, e.g. by hydrolysis.

The compounds of formula I may be isolated and purified using conventional techniques.

The conversion of free acids into salts and solvates and vice versa is carried out in conventional manner, solvates being formed, for example, by recrystalisation from, e.g. water or ethanol.

The pyrazole nucleus may exist in tautomeric forms:

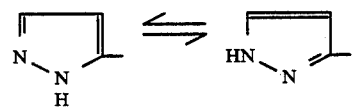

The position of the tautomeric equilibrium will of course depend on known factors such as temperature, aggregation condition, solvent and pH. Naturally, the invention is not limited to any particular tautomeric form.

The group —OCH₂COOH in the compound of the invention may be in the syn or anti-configuration. It is to be understood that the invention includes both isomeric forms as well as mixtures thereof. The syn isomers or isomeric mixtures in which the syn isomer predominates, e.g. to the extent of at least 75%, more particularly at least 90%, are however preferred.

If starting materials are employed in the form of syn isomers, then the product may be a syn isomer or a mixture of the syn and an anti-isomer, depending on the reaction conditions. Individual isomers may be isolated from mixtures by chromatographic methods.

Chromatographic separation may be effected in conventional manner, for example by column chromatography with a suitable eluant, e.g. acetonitrile/water or chloroform/methanol. The uniform fractions may be pooled and purified.

The intermediates of formula III can be prepared, for example, according to the following reaction scheme:

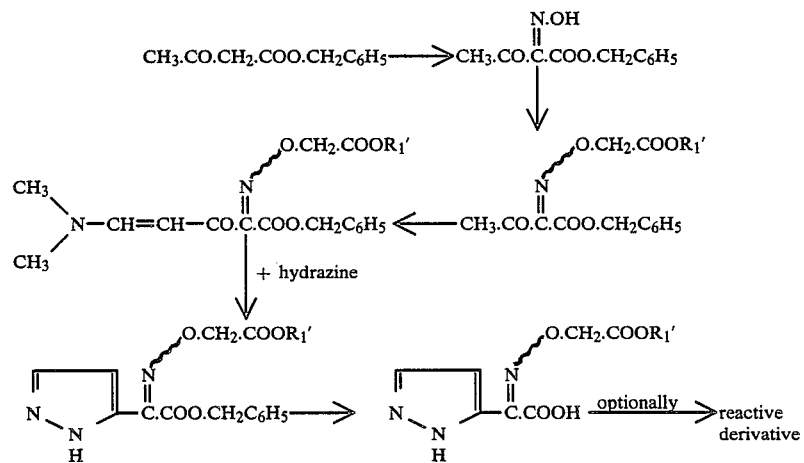

or, for example, analogously to the methods described in GB Patent Application No. 8004696 (Publication No. 2046734 A) or European Patent Application No. 81810118 (Publication No. 0037380).

A particularly interesting group of intermediates are those of the formula IIIa.

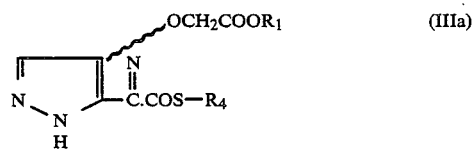

(IIIa)

wherein $R_1$ is as defined for formula III and $R_4$ is a 2-benzothiazol group and salts thereof with bases.

These compounds are new and also form part of the invention. They can be prepared analogously to the methods described in European Patent Application No. 81810118.

The compound of formula I is useful as chemotherapeutic agent, in particular anti-microbial agent, as indicated by its inhibiting effect against various bacteria, e.g. *Staphylococcus aureus, Streptococcus pyogenes, Streptococcus faecalis, Escherichia coli, Proteus vulgaris, Proteus mirabilis, Proteus morganii, Shigella dysenteria, Shigella sonnei, Shigella flexneri, Alcaligenes, faecalis, Klebsiella aerogenes, Klebsiella pneumoniae, Serratia marcescens, Salmonella Heidelberg, Salmonella typhimurium, Salmonella enteritidis,* and *Neisseria gonorrhoae,* in vitro in the series dilution test at concentrations of, for example, 0.01 to 50 μg/ml, and in vivo in the mouse at dosages of, for example, about 0.1 to 100 mg/kg of animal body weight. The compound is therefore useful as anti-bacterially active antibiotics particularly against gram-negative bacteria.

For this use, the effective dosage will, of course, vary depending on the particular compound employed, mode of administration and the treatment desired. However, in general, satisfactory results can be obtained when the compound is administered at a daily dosage of from about 10 to 100 mg/kg of animal body weight, suitably given in divided doses two to four times daily. For most larger mammals, the total daily dose is from about 1 to 6 g, more usually 3 to 6 g and dosage forms suitable for internal administration suitably contain 250 to 3000 mg, more usually 1000 to 3000 mg of the compound in admixture with a solid or liquid pharmaceutical carrier or diluent.

The compound of formula I may be administered in similar manner to known cephalosporins for use in such indications.

The suitable daily dosage for a particular compound will depend on a number of factors such as its relative potency of activity. It has, for example, been determined in mice with induced *E. coli* Septicaemia that, on subcutaneous administration, the compound of formula I, in the form of its di-sodium salt, has an $ED_{50}$ value of 0.1 mg/kg animal body weight.

In addition to this activity the compound of formula I exhibits a synergistic effect on polymorphonuclear leucocytes (PMNs) Thus pretreatment of a subject with an *E. coli* infection using a compound according to the invention, even at a dosage level below the inhibitory level of the compound itself, greatly enhances the killing effect of PMNs. It is believed that this effect is caused by modification of the bacterial surface by the compound. This effect was previously unknown for cephalosporins.

This can be demonstrated in vitro by opsonizing bacterial cultures in the exponential growth phase with various concentrations of the test substance (including those below the inhibitory level) and, after incubation for 30 minutes at 37° C., exposing these to a culture of rabbit PMNs and 1 hour later comparing the number of surviving cells with the number of cells in initial and untreated cultures. In vivo, the effect can be demonstrated by determining the effect of administration of the test substance on groups of mice infected by various bacteria whereby one of each pair of groups employed per bacteria and substance concentration is pretreated with the immunosuppressant, Cyclophosphamide, to reduce the number of functioning PMNs to maximally 10% of normal.

The compound of formula I may be employed in free acid form or in the form of a chemotherapeutically acceptable salt thereof, with a base or in the form of a chemotherapeutically acceptable solvate thereof, which forms have the same order of activity as the free acid. Suitable salt forms include alkali and alkaline earth metal and ammonium or amino acid salt forms. Suitable solvates are, for example, hydrates and ethanolates.

The compounds may be admixed with conventional chemotherapeutically acceptable diluents and carriers, and administered in such forms as tablets or capsules or, particularly, parenterally. Such compositions also form part of the invention.

The invention therefore also concerns a method of combatting bacteria comprising administering to a subject in need of such treatment an effective amount of a compound of formula I or a chemotherapeutically acceptable salt thereof, with a base or a chemotherapeutically acceptable solvate thereof and such compounds for use as chemotherapeutic agents, in particular antibacterially active antibiotics.

The following examples illustrated the invention. All temperatures are in degrees centigrade.

EXAMPLE 1

7-[(carboxymethoximino)-1H-pyrazol-3-yl-acetyl]amino-3-desacetoxy-3-(1-methyl-1H-tetrazol-5-yl-thio)cephalosporanic acid (syn-isomer; compound No. 1)

(a)(i)
7-[(tert.butoxycarbonylmethoximino)-1H-pyrazol-3-yl-acetyl]amino-3-desacetoxy-3-(1-methyl-1H-tetrazol-5-yl-thio)cephalosporanic acid (syn-isomer)

11 g of (tert.butoxycarbonylmethoximino)-1H-pyrazol-3-ylacetic acid (syn-isomer) are suspended with 19.8 g of 2,2′-dithiodipyridine in 200 ml of anhydrous dichloromethane and mixed, with stirring, with a solution of 24 g of triphenylphosphine in 200 ml of anhydrous dichloromethane. Upon completion of addition, stirring is continued for 4 hrs. at room temperature. At the same time 14 g of 3-desacetoxy-3-(1-methyl-1H-tetrazol-5-yl-thio)cephalosporanic acid are taken into solution in 200 ml of anhydrous dichloromethane with the aid of 7.15 ml of 1,5-diazabicyclo[5.4.0]undec-5-ene. The two solutions are combined and stirred for 15 hrs. at room temperature. The solvent is removed in vacuum, the residue taken up in 500 ml ethyl acetate and 100 ml water, the phases separated and the aqueous phase washed 10× with 100 ml portions of ethyl acetate which are then discarded. The remaining aqueous phase is decolourized with active carbon and then acidified to pH 1.5 with conc. hydrochloric acid. Careful extraction with ethyl acetate, drying of the extracts and evaporation of the solvent yields an oily residue, which is made filterable by digesting with 100 ml of ether. The title compound is obtained m.p. 155° (decomp).

NMR (DMSO): 9.45(d, 9 Hz, 1H); 7,78(d, 2.7 Hz, 1H); 6.5(d, 2.7 Hz, 1H); 5.87(dd, 9 Hz, 4.8 Hz, 1H); 5.18(d, 4.8 Hz, 1H); 5.59 (s, 1H); 4.42(d, 13 Hz, 1H); 4.23(d, 13 Hz, 1H); 3.95(s, 3H); 3.82(d, 18 Hz, 1H); 1,44(s, 9H).

(a)(ii)
7-[(ethoxycarbonylmethoximino)-1H-pyrazol-3-yl-acetyl]amino-3-desacetoxy-3-(1-methyl-1H-tetrazol-5-yl-thio)cephalosporanic acid (syn-isomer)

This compound can be prepared analogously to (a)(i) above or as follows:

(i) 7.85 g of triphenylphosphine, 10 g of bis-benzthiazolyldisulfide and 62.5 ml of methylenechloride are stirred overnight at 20° to 25°. The mixture is then cooled to 0° to 5° and 6.025 g of (ethoxycarbonylmethoximino)-1H-pyrazol-3-yl-acetic acid added in portions such that the temperature does not rise above 5°. After completion of the addition the mixture is stirred for 4 hours at 0° to 5°.

(ii) 8.05 g of tetrazolyl ACA are suspended in 62.50 ml of methylenechloride and 650 ml of bis-trimethyl silylacetamide added dropwise under water-cooling. The mixture is then stirred at 20° to 25° until the tetrazolyl-ACA has dissolved (ca. 3 hours). The resulting solution is cooled to −10° and the active ester obtained above added thereto. Stirring is continued for 4 hours at 0° to 5° and the mixture then allowed to stand overnight in a cool room at 3°.

The mixture is added to 60 ml of cold water (0° to 5°) and 26 ml of NaHCO$_3$ solution slowly added under cooling. The methylenechloride phase is then separated and re-extracted and the combined aqueous phases extracted with methylenechloride.

The aqueous solution is covered with a layer of 16 ml of tetrahydrofuran and 64 ml of ethyl acetate and then semiconc. HCl added dropwise with vigurous stirring until a pH of 2 is achieved. The resulting aqueous phase is then reextracted with tetrahydrofuran and ethylacetate.

The combined organic phases are washed with saturated salt solution. 5 g of sodium sulphate and 4 g of active charcoal are added and after stirring and filtering the solution is concentrated on a rotary evaporator. The oily residue is mixed with diisopropyl ether and again concentrated in vacuum. The residual light brown oil is dissolved in methylene chloride and mixed with isopropanol. After stirring the mixture is filtered and the product evaporated to dryness in vacuum to produce the title product m.p. 119°-123° (decomp.).

The sodium salt can be prepared by suspending the acid in dioxane reacting with sodium ethylhexanoate solution and working up by precipitation, filtration, washing and drying.

(b)(i) 5 g of 7-[(tert.butoxycarbonylmethoximino)-1H-pyrazol-3-yl-acetyl]amino-3-desacetoxy-3-(1-methyl-1H-tetrazol-5-yl-thio)cephalosporanic acid (syn-isomer) are added slowly, at room temperature to 50 ml of anhydrous trifluoroacetic acid and stirred for 2 hrs. at room temperature. The resulting reaction mixture is evaporated to dryness at room temperature and the residue mixed with 100 ml of ether. The precipitate is filtered, washed with ether and dried to yield the title product (compound No. 1)=M.p. 128°-131°.

(b)(ii) 1.44 g of 7-[(ethoxycarbonylmethoximino)-1H-pyrazol-3-yl-acetyl]amino-3-desacetoxy-3-(1-methyl-1H-tetrazol-5-yl-thio)cephalosporanic acid (syn-isomer) are stirred for 15 hrs. in 40 ml of water with 5.2 ml of 1N caustic soda. The resulting solution is acidified and extracted with ethyl acetate to yield the title product (compound No. 1). M.p. 128°-131°.

EXAMPLE 2

7-[(carboxymethoximino)-1H-pyrazol-3-yl-acetyl-]amino-3-desacetoxy-3-(1-methyl-1H-tetrazol-5-yl-thio)cephalosporanic acid disodium salt (syn-isomer; compound No. 2)

(a) Mono-sodium salt 270 g of 7-[(carboxymethoximino)-1H-pyrazol-3-yl-acetyl]amino-3-desacetoxy-3-(1-methyl-1H-tetrazol-5-yl-thio)cephalosporanic acid (syn-isomer) are dissolved in 1,500 ml of ethanol and 500 ml of acetone. 750 ml of a 1 mol solution of sodium ethyl hexanoate in isopropanol are added dropwise over 2 hrs. After the addition of 70 ml (25 mins) the sodium salt begins to precipitate and the solution is cooled to 5°. After the addition is completed 2½ l. of isopropanol are added and the mixture is allowed to stand for 2 hrs. Then the mixture is filtered, washed twice with 1,000 ml of isopropanol and ether and filtered again. After drying for 4 days in high vacuum the mono-sodium salt is obtained in the form of a white powder.

(b) Di-sodium salt

The mono-sodium salt is dissolved in water and the pH value is adjusted to 7.0 adding 0.1N NaOH. Freeze-drying of this solution gives the di-sodium salt (compound No. 2).

NMR ($D_2O$): 7.82 (d, J=1.9 Hz, 1H); 6.75 (d, J=1.9 Hz, 1H); 5.88 (d, J=4 Hz, 1H); 5.22 (d, J=4 Hz, 1H); 4.65 (s, 2H); 4.22 (ABq, J=13.5 Hz, 2H); 4.05 (s, 3H); 3.65 (ABq, J=18 Hz, 2H).

EXAMPLE 3

7-[(carboxymethoximino)-1H-pyrazol-3-yl-acetyl-]amino-3-desacetoxy-3-(1-methyl-1H-tetrazol-5-yl-thio)cephalosporanic acid ethanol solvate (synisomer; compound No. 3)

5 g of 7-[(carboxymethoximino)-1H-pyrazol-3-yl-acetyl]amino-3-desacetoxy-3-(1-methyl-1H-tetrazol-5-yl-thio)cephalosporanic acid syn-isomer are dissolved in 50 ml of ethanol at 20°, the solution is filtered and the filtrate cooled to 0° over 20 hrs. The precipitate is filtered and dried at 0.05 bar/30° over 30 hrs. This gives the ethanol solvate in the form of white crystals. M.p. 137° (decomp.)

IR (KBr): 3429, 3236, 2967, 2725, 2525, 2427, 2333, 1776, 1712, 1675, 1630, 1544, 1401, 1366, 1244, 1239, 1176, 1118, 1093, 1065, 1023, 1001, 979, 930, 875, 808, 780, 698.

NMR (DMSO): 9.49 (d, J=9 Hz, 1H, NH); 7.78 (d, J=1.9 Hz, 1H, pyrazole-$H_4$); 6.51 (d, J=1.9 Hz, 1H, pyrazole-$H_5$); 5.89 (dd, $J_1$=9 Hz, $J_2$=4.5 Hz, 1H, $H_7$); 5.17 (d, J=4.5 Hz, $H_6$); 4.31 (ABq, J=12.6 Hz, $H_3$); 4.64 (s, 2H, $OCH_2COOH$), 3.95 (s, 3H, $NCH_3$); 3.71 (ABq, J=18 Hz, 2H, $H_2$); 3.48 (q, J=7.2 Hz, 2H, $OCH_2CH_3$); 1.05 (t, J=7.2 Hz, 3H, $OCH_2CH_3$).

Analogously to the above procedure or by other conventional methods, the following further salts may be obtained.

| Compound No. | Salt | Physical data |
|---|---|---|
| 4 | calcium | 170° (decomp.) |
| 5 | magnesium | 180° (decomp.) |
| 6 | di-lysine | 170° (decomp.) |
| 7 | di-arginine | 160° (decomp.) |
| 8 | di-ethanolamine | 100° (decomp.) |

The required starting materials can be prepared, for example, as follows:

A.
(tert.Butoxycarbonylmethoximino)-1H-pyrazol-3-yl-acetic acid (syn isomer)

(a) Oximinoacetoacetic acid benzyl ester 450 g of Sodium nitrite in 600 ml of water are added dropwise, at 0° over 3 hrs. to a solution of 1000 ml acetoacetic acid benzylester (benzylacetate) in 1000 ml of glacial acetic acid and the mixture stirred for 18 hrs. at room temperature. After the addition of 3000 ml of water the mixture is extracted three times with 1500 ml portions of dichloromethane. The combined extracts are washed twice with 500 ml portions of water. Potassium carbonate is added with thorough stirring until the aqueous phase is neutral. The organic phase is separated, dried with magnesium sulphate and the solvent removed in vacuum. The residue is taken up in 5000 ml of di-isopropyl ether, the insoluable material filtered off and the solution again evaporated to dryness. Trituration with petroleum ether and filtration yields the title product.

(b) tert.Butoxycarbonylmethoximinoacetoacetic acid benzyl ester

Over a period of 3 hrs. 293 ml of bromoacetic acid tert.butyl ester are added dropwise, with stirring to a solution of 442 g of oximinoacetoacetic acid benzyl ester and 420 ml of triethylamine in 2000 ml of dimethylsulphoxide. This causes the temperature to rise to 40°. Stirring is continued for 12 hrs. and the resulting mixture poured into ice-water and extracted three times with 1500 ml portions of petroleum ether. The combined extracts washed in sequence with 200 ml of 1N hydrochloric acid (3×), 500 ml of water, 500 ml of 1N sodium hydroxide (3×) and saturated salt solution (2×), dried over magnesium sulphate and concentrated in vacuum. The title product is obtained as a light yellow oil.

(c) N,N-dimethylaminoacryloyl-tert.butoxycarbonylmethoximino acetic acid benzyl ester 560 g of tert.butoxycarbonylmethoximino acetic acid benzylester and 450 ml of dimethylformamide-dimethylacetal are heated for 4 hrs. at 110° to 500 ml of toluene and then stirred for 15 hrs. at room temperature. Evaporation to dryness yields raw title product as a dark oil, which can be purified by chromatography on kieselgel to light yellow crystals. m.p. 56°.

(d) (tert.Butoxycarbonylmethoximino)-1H-pyrazol-3-yl-acetic acid benzyl ester (syn-isomer)

The dark oil obtained according to (A)(c) is dissolved in 200 ml of ethanol and stirred at room temperature for 12 hrs. with a solution of 200 g of hydrazine hydrate and 450 g of glacial acetic acid in 1000 ml ethanol. The resulting mixture is concentrated to dryness and the residue taken up in 10 l of diisopropyl ether and 2 l of water. The organic phase is washed with 500 ml water (3×), 500 ml 1N sodium hydroxide (3×), 500 ml 1N hydrochloric acid (3×), water and finally with saturated salt solution, dried over magnesium sulphate and concentrated to a volume of ca. 1000 ml. After addition of 4 l of petroleum-ether, the mixture is allowed to stand over night and the precipitate filtered and dried. M.p. 71°.

(e) (tert.-Butoxycarbonylmethoximino)-1H-pyrazol-3-yl-acetic acid (syn-isomer)

470 g of (tert.butoxycarbonylmethoximino)-1H-pyrazol-3-yl-acetic acid benzylester (syn-isomer) are hydrogenated in 4 l of methanol over 5 g of Pd/C. After filtration of the catalyst the solvent is removed in vacuum and the crystalline residue digested with di-isopropylether. The title product is thus obtained. M.p. 138°-140° (decomp.).

B. Proceeding analogously to example A, via the following intermediates:

(a) 2-hydroxyiminoacetoacetic acid tert.butyl ester. m.p. 55°-60°;

(b) 2-ethoxycarbonylmethoximinoacetoacetic acid tert.butyl ester. b.p. 122°-125°/0.4 mbar;

(c) 4-dimethylaminomethylen-2-ethoxy-carbonylmethoximino-acetic acid tert.butyl ester. m.p. 60°-62°;

(d) (ethoxycarbonylmethoximino)-1H-pyrazol-3-yl-acetic acid tert.butyl ester. m.p. 82°-84°
there may be obtained (ethoxycarbonylmethoximino)-1H-pyrazol-3-yl-acetic acid. m.p. 138°-140°.

We claim:

1. The process for preparing a compound

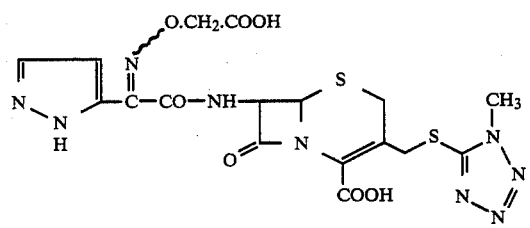

and salts thereof with bases as well as solvates thereof, comprising reacting a compound of the formula II:

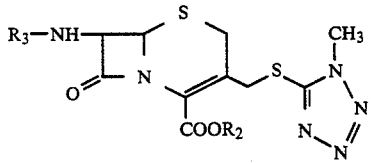

wherein $R_3$ represents hydrogen or an amino protecting group and $R_2$ represents hydrogen, an easily removable ester group or other carboxyl protecting group, with a compound of formula IIIa,

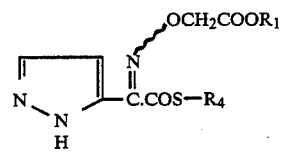

wherein $R_1$ represents hydrogen, an easily removable ester group or other carboxyl protecting group, and $R_4$ is a 2-benzothiazol group, and salts thereof with bases, and if required removing any ester group or protecting group to produce a compound of formula I in free acid form, and recovering the compound of formula I in free acid form or in the form of a salt thereof with a base or in the form of a solvate.

2. A compound of the formula:

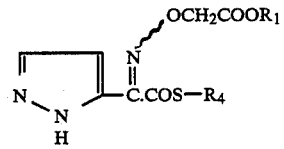

wherein $R_1$ is a hydrogen atom, an easily removable ester group or other carboxyl protecting group, and $R_4$ is a 2-benzothiazol group; or a salt thereof with a base.

* * * * *